United States Patent [19]

Cameron et al.

[11] Patent Number: 4,929,787
[45] Date of Patent: May 29, 1990

[54] PROCESS FOR CONVERTING METHANE TO HIGHER HYDROCARBONS

[75] Inventors: Charles Cameron, Paris; Hubert Mimoun, Rueil Malmaison; Serge Bonnaudet, Paris; Alain Robine, Rueil Malmaison, all of France

[73] Assignee: Institut Francais du Petrole, Rueil-Malmaison, France

[21] Appl. No.: 228,341

[22] Filed: Aug. 4, 1988

[30] Foreign Application Priority Data

Aug. 5, 1987 [FR] France ............................ 87 11183
Nov. 27, 1987 [FR] France ............................ 87 16614

[51] Int. Cl.$^5$ ............................ C07C 2/00; C07C 5/00
[52] U.S. Cl. .................................... 585/500; 585/654; 585/656; 585/661; 585/750; 585/943
[58] Field of Search ............... 585/500, 943, 654, 656, 585/661, 750

[56] References Cited

U.S. PATENT DOCUMENTS

| | | | |
|---|---|---|---|
| 4,499,323 | 2/1985 | Gaffney | 585/500 |
| 4,499,324 | 2/1985 | Gaffney | 585/500 |
| 4,568,789 | 2/1986 | Withers, Jr. | 585/661 |
| 4,593,139 | 6/1986 | Withers | 585/661 |

FOREIGN PATENT DOCUMENTS

| | | | |
|---|---|---|---|
| 0189079 | 7/1986 | European Pat. Off. | 585/700 |
| WO85/04866 | 11/1985 | World Int. Prop. O. | 585/700 |
| WO86/07351 | 12/1986 | World Int. Prop. O. | 585/500 |

*Primary Examiner*—Patrick P. Garvin
*Assistant Examiner*—E. D. Irzinski
*Attorney, Agent, or Firm*—Millen, White & Zelano

[57] ABSTRACT

The invention concerns a process for the oxidative conversion of methane or natural gas to higher hydrocarbons, particularly ethylene and ethane, characterized in that a methane-oxygen mixture is passed over a contact mass consisting of at least one compound pertaining to the family of rare-earth metal carbonates. It concerns particularly the use of rare-earth oxycarbonates, more particularly lanthanum oxycarbonate $La_2O_2(CO_3)$, as contact mass.

20 Claims, No Drawings

PROCESS FOR CONVERTING METHANE TO HIGHER HYDROCARBONS

The present invention concerns a process for the oxidative conversion of methane or natural gas to higher hydrocarbons, particularly ethylene and ethane, characterized in that a mixture of methane and oxygen is passed over a contact mass formed of at least one compound pertaining to the family of rare-earth metal carbonates. By "carbonates" it is meant both simple carbonates and oxycarbonates.

BACKGROUND OF THE INVENTION

Many attempts have been made for converting methane to higher hydrocarbons, particularly to ethylene. As a matter of fact, the direct conversion of methane to ethylene is highly desirable, since ethylene may be used as raw material for the synthesis of various important products.

Much research has have been devoted to the oxidizing methane coupling reaction according to the scheme:

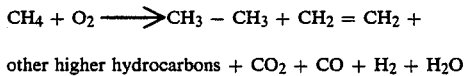

other higher hydrocarbons + $CO_2$ + $CO$ + $H_2$ + $H_2O$

This reaction may be performed, depending on the type of catalyst, either in the simultaneous mode (passing a $CH_4+O_2$ mixture over a catalyst) or the sequential mode (methane oxidation to higher hydrocarbons by means of a reducible agent, followed by the reoxidation of said agent by oxygen of air).

For the oxidizing coupling in the sequential mode, two patents (U.S. Pat. No. 4,499,323 and U.S. Pat. No. 4,523,049) indicate the use of praseodymium oxide, $Pr_6O_{11}$, as reducible agent at a temperature from 700° to 800° C.

For the oxidizing coupling in the simultaneous mode, certain works indicate the use of rare-earth oxides, particularly: Otsuka and Coll. in a series of articles (*Chemistry Letters*, 1985, p. 499; 1986, p. 467; 1987, p. 483; *J. Catalysis*, 1986, 100, p. 353) and Imai in an article (*J. Chem. Soc. Chem. Comm.*, 1986, p. 52) have mentioned the use of rare-earth oxides as catalysts for methane oxidative coupling, with long contact times and preferably in the presence of a large excess of inert gas diluent.

The use of rare-earth oxides alone is disclosed in two patents (European patent 189 079 and World patent 8 607 351), and the use of rare-earth oxides doped with alkali metals is also disclosed in two patents (European patent 206 044 and World patent 8 607 351).

One disadvantage of the use of the above-mentioned catalysts results from their quick deactivation due to sintering phenomena, to the loss of volatile or liquid constituents such as alkali metals, or to coke deposition. Another disadvantage of the above-mentioned catalysts results from their low activity, requiring the use of high catalyst amounts, of long contact times and of a very high temperature, generally higher than 750° C.

SUMMARY OF THE INVENTION

A new family of contact masses has now been discovered, whereby the activity, the selectivity and the stability to methane oxidative coupling products are increased. By use of these contact masses higher conversion rates at lower temperatures are obtained and it is possible to operate with high feeding rates of reactant gases and hence with low reaction volumes.

The contact masses used in the process according to the invention are characterized in that they contain, as essential active element, at least one rare-earth metal carbonate. The term carbonates includes simple carbonates and oxycarbonates.

The rare-earth metal carbonates may be characterized by elementary analysis and by infra-red and X-ray spectroscopy methods. They comply approximately with the general formulas:

$$M_2(CO_3)_3$$
$$M_2O_2(CO_3)$$
$$M_2O(CO_3)_2$$
$$M(OH)(CO_3)$$

In the above-mentioned formulas, each M, identical or different, is any metal from the rare-earth group such as lanthanum, praseodymium, neodymium, samarium, europium, gadolinium, terbium, dysprosium, holmium, erbium, thulium, ytterbium and lutetium. Lanthanum, neodymium and samarium are preferred. Lanthanum is the most preferred. Interesting contact masses are those corresponding to the following formula:

The preparation of rare-earth oxycarbonates may be performed by thermal decomposition of carboxylates complying with the formula $M(O_2CR)_3$, as disclosed in the book "Gmelin Handbook of Inorganic Chemistry" 8th Edition-Sc, Y, La to Lu Carboxylates, Volume D5 (1984). In this formula, R may consist entirely of hydrocarbons or contain aromatic groups and/or heteroatoms such as oxygen. Carboxylic monoacids, carboxylic polyacids, carboxylic acid-alcohols, carboxylic acid-ketones, can be used.

The thermal decomposition of the rare-earth carboxylate precursors may be performed outside the reactor or in the reaction zone before passing the reacting gas mixture over the contact mass. This decomposition is achieved at a temperature ranging from about 300° to 700° C., depending on the starting compound. The formation of the desired compound can be ascertained by infra-red analysis, for example. A total conversion to oxide must however be avoided.

It has been discovered that the addition of one or more alkaline-earth metal compounds to the above-mentioned rare-earth metal carbonates, gives a better selectivity to $C_2+$ products (ethane, ethylene and other higher hydrocarbons) without loss of activity. The contact masses containing alkaline-earth compounds and rare-earth metal carbonates conform approximately with the following formula:

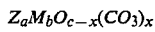

In this formula, Z represents one or more alkaline-earth metals such as beryllium, magnesium, calcium, strontium and barium, M represents one or more rare-earth metals, a=0.001 to 2, b=2, c=3+a, x=0.1 to c. Preferred rare-earth metals are lanthanum, neodymium and samarium, alone or as mixture. Lanthanum is preferred. Interesting contact masses are those corresponding to the following formula:

$Z_aM_2O_2(CO_3)_{1+a}$

In this formula, Z represents one or several alkaline-earth metals, M one or several rare-earth metals and the value of a is from 0.001 to 2. Preferred rare-earth metals are lanthanum, neodymium and samarium, the most convenient being lanthanum.

It has also been found that the addition of a group IVA metal to the carbonate contact mass leads to an increased activity in the oxidative coupling reaction. The contact masses containing alkaline-earth metals, group IVA compounds and rare-earth carbonates correspond approximately to the following formula:

$Z_aM'_dM_bO_{c-x}(CO_3)_x$ wherein Z represents one or more alkaline-earth metals, M' represents one or more metals from group IVA such as titanium, zirconium and hafnium, M represents one or more rare-earth metals, a ranges from 0.001 to 2, $b=2, c=3+a+2d-z$, d=0.001 to 2, x=0.1 to c, z=0 to 0.5 d. In this formula, z has a value from 0 to 0.5d, hence z is zero when the oxidation level of all the metals from group IVA is +4, 0.5 d when the oxidation level of these metals is +3, and in the range from 0 to 0.5 d in the presence of a mixture of +3 and +4 oxidation levels. Preferred rare-earth metals are lanthanum, neodymium and samarium, more particularly lanthanum.

The invention is however not limited to the above formulas. As a matter of fact, the beneficial effect of the presence of alkaline earth-metals and optionally of group IVA metals is obtained irrespective of the form in which these metals are present, although it is preferred to use them as oxide and/or carbonate.

The above-described contact masses, such as rare-earth metal carbonates and oxycarbonates, optionally containing alkaline-earth metal compounds or containing both alkaline-earth metal compounds and group IVA metal compounds, may be prepared according to different methods and used either as such or on a carrier. Inert carriers (such as silica, magnesia, calcium oxide, zinc oxide and alpha alumina) and active carriers (such as rare-earth perovskites, spinelles and pyrochlores) are convenient.

The following non-limitative examples illustrate various methods of preparation which can be used to obtain the preferred contact masses. For example, mixtures of rare-earth metal and alkaline-earth metal hydroxides, nitrates, carbonates or carboxylates may be added to a solution of polycarboxylic acid such as citric acid. The formed citrates may be thermally dried under vacuum and then roasted under vacuum or in the presence of air within a temperature range from about 300° to 700° C., so as to generate the desired carbonate contact mass.

Another preparation method consists of thermally decomposing a mixture of rare-earth metal carbonates and alkaline-earth metal carbonates or oxides at a temperature from 300° to 700° C.

Another example of preparation of carbonate contact masses consists of extruding aqueous suspensions of rare-earth metal carbonates and alkaline-earth metal carbonates or oxides.

Still another example of carbonate contact masses preparation consists of admixing rare-earth and alkaline-earth metal carbonates, hydroxides and/or oxides in an acid such as acetic acid. The acid mixture is then thermally dried and decomposed in air at temperatures ranging from about 300° to 700° C.

Another method for preparing the desired carbonate contact mass consists of dissolving rare-earth metal or alkaline-earth metal carbonates or acetates or other carboxylates into an aqueous solution of formic, acetic or other carboxylic acid and of impregnating with said solution an inert carrier such as silica, magnesia, calcium oxide, zinc oxide or alpha alumina, or an active carrier such as $MAlO_3$ or $M_ySr_{1-y}TiO_4$ (M being a rare-earth and y ranging from 0.5 to 1) or other rare-earth-containing perovskites spinelles or rare-earth pyrochlores (such as $M_2Si_2O_7$), by dry impregnation technique, i.e. by a solution volume substantially equal to the pore volume. The so-prepared carbonates are then heated in air at a temperature ranging from about 300° to 700° C.

By way of example, the carbonate contact masses can be prepared by extracting alkaline-earth metal carbonate over a rare-earth metal carbonate and then heating the carbonate mixture in air within a temperature range from about 300° to 700° C.

In another example, the carbonate contact masses are prepared by admixing rare-earth metal oxides with alkaline-earth metal carbonates, oxides or nitrates, and by contacting this mixture with a carbon dioxide-containing gas. These non-limiting examples are also applicable to contact masses containing nitrates, hydroxides, carboxylates, carbonates and oxides of group IVA metals.

The above-mentioned contact masses have the advantage of providing for an oxidative conversion of methane with a high selectivity to higher hydrocarbons and with a very high activity. Another advantage of the above-mentioned carbonate contact masses is to provide for a high oxygen conversion. These contact masses have the further advantage of being very stable and of being free of alkali metals, known to generating a rapid decrease of the catalytic activity, as a result of the formation of carbonates of low melting point. The above-mentioned contact masses still have the further advantage of not producing coke or soot.

The reaction according to the invention is performed by contacting a methane(or natural gas)-oxygen mixture with the contact mass in solid state. The oxygen may be pure or diluted with an inert gas such as nitrogen (as air), carbon dioxide and steam. For safety reasons, the oxygen amount contained in methane cannot exceed 40% by mole. It may thus range from 0.1 to 40%, preferably from 5 to 25% by mole.

It has been found that a higher yield to coupling products can be obtained by adding steam to the methane- and oxygen-containing gas. Advantageously, 0.1 to 25%, preferably about 0.1 to 10% by mole of water, will be added to the reacting gas.

The addition of carbon dioxide gas to the methane- and oxygen-containing gas also results in higher yields to coupling products. Carbon dioxide acts both as diluent and as constituent used to maintain a high activity of the carbonate contact mass. It is hence beneficial to add a carbon dioxide amount of about 0.1 to 20%, preferably about 0.1 to 8% by mole to the reacting gas.

It is also possible to use several reaction zones in series, with introduction of a controlled oxygen amount at each stage in the gas feeding the reactors.

The reaction temperature, with the contact masses according to the invention, is generally from 300° to 950° C., for example from 300° to 900° C., preferably from 550° to 900° C., particularly 550°–750° C.

The total pressure in the reactor may be for example from 1 to 100 bars, particularly 1–20 bars. The contact time is from $10^{-6}$ sec. to 10 sec., preferably from $10^{-5}$ sec. to 1 sec.

EXAMPLES

The following examples are given to illustrate the invention and must not be considered as limiting the scope thereof. In these examples, the reactions are conducted according to the following operating mode:

In a vertical tubular reactor, made of sintered alumina, of 800 mm length and 15 mm diameter, placed and centered into a tubular furnace of 500 mm length and 60 mm diameter, a 2 ml contact bed is introduced between two quartz-wool plugs. This contact bed comprises the contact mass diluted with quartz particles (of size ranging from 0.1 to 0.2 cm) located at 6 cm from the tubular furnace bottom, and the reactor filling is completed with quartz particles of the same size.

Before passing the methane-oxygen mixture, the contact bed is treated with a stream of helium at 525° C. for 1 hour at a flow rate of 900 ml/min., so as to convert the precursor to active compound.

The gas mixture of 95% methane and 5% oxygen molar content is introduced at the top of the reactor and preheated in the packing of quartz particles before passing through the contact bed. The gas effluent is analyzed on line at the reactor output by gas chromatography. The reactor temperature is measured within the contact bed.

EXAMPLES 1–5

Examples 1 to 5 are given for comparison purpose and illustrate the selectivity of the products at various temperatures for a contact mass formed of 0.800 g pure lanthanum oxide (4.91 mmoles) diluted with 2 ml of quartz particles. $La_2O_3$ was prepared by thermal decomposition of hydrated lanthanum acetate $La(O_2CCH_3)_3, 1.5\ H_2O$, under a stream of gas formed of 80% nitrogen and 20% oxygen, at 900° C. for 18 hours. This operating mode gives a $La_2O_3$ essentially free of carbonate.

The temperatures, flow rates and analysis results of the gas effluent are reported in table 1.

EXAMPLES 6–10

Examples 1–5 are repeated, but the reactor is charged with 1.550 g of anhydrous lanthanum acetate $La(O_2CCH_3)_3$ (4.90 mmole) diluted with 2 ml of quartz particles. After treatment of the contact bed with helium at 525° C. for 1 hour, lanthanum acetate is converted to lanthanum oxycarbonate $La_2O_2(CO_3)$, as determined by infra-red analysis.

As shown in table 2, the use of lanthanum oxycarbonate instead of lanthanum oxide, results in higher methane conversion and selectivity to coupling products, particularly at lower temperature.

EXAMPLES 11–15

Examples 6–10 are repeated but with half the amount of lanthanum acetate precursor, i.e. 0.800 g, diluted with 2 ml of quartz particles, giving lanthanum oxycarbonate after thermal treatment at 525° C. The temperature is brought to 700° C. and the oxygen concentration in methane is varied as well as the flow rates.

As shown in table 3, the contact mass of these examples is very active for methane oxidizing coupling, even at very high flow rates of gas mixture. The increased oxygen content only results in a small decrease of the selectivity for a high conversion to methane. Thus, for a 12% oxygen molar content of methane, the methane conversion rate is 17.7% and the selectivity to ethane+ethylene is 68.1%.

EXAMPLES 16–18

Examples 11–15 are repeated but the reactor is charged with a mixture of lanthanum oxide (0.400 g) and lanthanum acetate (0.775 g), which, after heating at 525° C., is converted to $La_2O_2(CO_3)$.

Table 4 shows that said combination of lanthanum solids improves the conversion to methane and the selectivity to ethane+ethylene as compared to the results obtained with lanthanum oxide alone (examples 1–5).

EXAMPLES 19–21

Examples 11–15 are repeated but the reactor is charged with 0.488 g of lanthanum oxycarbonate $La_2O_2(CO_3)$ obtained by thermal decomposition of $La(O_2CCH_3)_3$ in air at 525° C. in a muffle furnace for 1 hour, as determined by infra-red analysis.

The comparison of the results of examples 11 (table 3) and 21 (table 5), shows that, irrespective of the oxycarbonate formation inside or out of the reactor, the oxycarbonate leads to the same results for methane oxidative coupling.

EXAMPLES 22–25

Examples 22–25 show that lanthanum carbonates are not the only active lanthanides for converting methane to higher hydrocarbons. The preceding examples are repeated but the reactor is charged with 0.405 g (1.26 mmole) of neodymium acetate $Nd(O_2CCH_3)_3$, diluted with 2 ml of quartz particles. After conversion of the acetate to oxycarbonate by thermal treatment under helium at 525° C., the gas mixture (methane and oxygen) is introduced into the reactor. The results of the analyses, reported in table 6, show that neodymium oxycarbonate is also very active for converting methane to higher hydrocarbons.

EXAMPLES 26–29

Examples 22–25 are repeated but the reactor is charged with 0.589 g (1.23 mmole) of samarium carbonate $Sm_2(CO_3)_3$, diluted with 2 ml of quartz particles. As shown in table 7, samarium oxycarbonate forms a very active contact mass for methane oxidizing coupling.

EXAMPLES 30–33

The preceding examples are repeated but the reactor is charged with a mixture of 0.200 g of samarium carbonate, 0.200 g of neodymium acetate and 0.200 g of lanthanum acetate, diluted with 2 ml of quartz particles. Table 8 shows that a combination of rare-earth group metal oxycarbonates is also very active for converting methane to higher hydrocarbons.

TABLE 1

| EXAMPLE | 1 | 2 | 3 | 4 | 5 |
|---|---|---|---|---|---|
| Temperature (°C.) | 600 | 650 | 700 | 750 | 750 |
| Flow rate (ml/min) | 947 | 947 | 947 | 947 | 919 |
| $O_2$ % in the charge | 5.0 | 5.0 | 5.0 | 5.0 | 7.0 |
| $CH_4$ conversion % | 1.6 | 3.0 | 4.6 | 8.3 | 11.9 |
| $O_2$ conversion % | 36.4 | 43.2 | 57.8 | 82.6 | 89.1 |
| $CO_2$ selectivity % | 52.9 | 19.6 | 13.4 | 11.3 | 14.8 |
| CO selectivity % | 28.7 | 29.7 | 19.3 | 10.3 | 10.7 |
| $C_2H_4$ selectivity % | 0 | 1.2 | 7.9 | 22.8 | 27.9 |

TABLE 1-continued

| EXAMPLE | 1 | 2 | 3 | 4 | 5 |
|---|---|---|---|---|---|
| $C_2H_6$ selectivity % | 18.5 | 49.5 | 59.5 | 55.6 | 46.7 |
| $C_2$ yield × 100 | 0.29 | 1.48 | 3.13 | 6.51 | 8.85 |

TABLE 2

| EXAMPLE | 6 | 7 | 8 | 9 | 10 |
|---|---|---|---|---|---|
| Temperature (°C.) | 600 | 650 | 700 | 750 | 750 |
| Flow rate (ml/min) | 947 | 947 | 947 | 947 | 919 |
| $O_2$ % in the charge | 5.0 | 5.0 | 5.0 | 5.0 | 7.0 |
| $CH_4$ conversion % | 6.0 | 7.5 | 9.2 | 9.8 | 12.6 |
| $O_2$ conversion % | 91.2 | 94.3 | 98.5 | 99.4 | 100 |
| $CO_2$ selectivity % | 27.0 | 22.2 | 17.2 | 16.3 | 18.6 |
| CO selectivity % | 20.1 | 11.9 | 7.3 | 6.3 | 7.5 |
| $C_2H_4$ selectivity % | 6.6 | 16.1 | 24.0 | 29.0 | 31.2 |
| $C_2H_6$ selectivity % | 46.3 | 49.7 | 51.5 | 48.3 | 42.7 |
| $C_2$ yield × 100 | 3.17 | 4.94 | 6.95 | 7.58 | 9.31 |

TABLE 3

| EXAMPLE | 11 | 12 | 13 | 14 | 15 |
|---|---|---|---|---|---|
| Temperature (°C.) | 700 | 700 | 700 | 700 | 700 |
| Flow rate (ml/min) | 947 | 967.5 | 990 | 1980 | 1023 |
| $O_2$ % in the charge | 5.0 | 7.0 | 9.1 | 9.1 | 12.0 |
| $CH_4$ conversion % | 8.7 | 11.8 | 14.8 | 12.9 | 17.7 |
| $O_2$ conversion % | 92.2 | 93.3 | 95.9 | 84.1 | 97.2 |
| $CO_2$ selectivity % | 14.5 | 15.6 | 18.0 | 15.8 | 21.7 |
| CO selectivity % | 8.4 | 9.0 | 10.3 | 11.9 | 12.4 |
| $C_2H_4$ selectivity % | 23.2 | 30.0 | 32.1 | 28.8 | 34.1 |
| $C_2H_6$ selectivity % | 53.9 | 45.5 | 39.5 | 43.5 | 34.0 |
| $C_2$ yield × 100 | 6.69 | 8.87 | 10.61 | 9.29 | 11.69 |

TABLE 4

| EXAMPLE | 16 | 17 | 18 |
|---|---|---|---|
| Temperature (°C.) | 600 | 650 | 700 |
| Flow rate (ml/min) | 947 | 947 | 947 |
| $O_2$ % in the charge | 5.0 | 5.0 | 5.0 |
| $CH_4$ conversion % | 6.5 | 8.4 | 9.2 |
| $O_2$ conversion % | 84.7 | 89.4 | 96.2 |
| $CO_2$ selectivity % | 19.9 | 15.1 | 14.7 |
| CO selectivity % | 16.6 | 10.8 | 8.9 |
| $C_2H_4$ selectivity % | 15.3 | 22.7 | 25.8 |
| $C_2H_6$ selectivity % | 48.2 | 51.3 | 50.7 |
| $C_2$ yield × 100 | 4.15 | 6.20 | 7.05 |

TABLE 5

| EXAMPLE | 19 | 20 | 21 |
|---|---|---|---|
| Temperature (°C.) | 600 | 650 | 700 |
| Flow rate (ml/min) | 947 | 947 | 947 |
| $O_2$ % in the charge | 5.0 | 5.0 | 5.0 |
| $CH_4$ conversion % | 5.4 | 6.8 | 8.6 |
| $O_2$ conversion % | 91.0 | 92.3 | 96.1 |
| $CO_2$ selectivity % | 31.2 | 17.9 | 12.8 |
| CO selectivity % | 27.9 | 16.6 | 9.7 |
| $C_2H_4$ selectivity % | 5.2 | 16.8 | 21.2 |
| $C_2H_6$ selectivity % | 35.8 | 48.6 | 56.2 |
| $C_2$ yield × 100 | 2.21 | 4.45 | 6.66 |

TABLE 6

| EXAMPLE | 22 | 23 | 24 | 25 |
|---|---|---|---|---|
| Temperature (°C.) | 550 | 600 | 648 | 699 |
| Flow rate (ml/min) | 947 | 947 | 947 | 947 |
| $O_2$ % in the charge | 5.0 | 5.0 | 5.0 | 5.0 |
| $CH_4$ conversion % | 5.0 | 6.5 | 7.5 | 8.1 |
| $O_2$ conversion % | 86.0 | 94.3 | 98.3 | 99.0 |
| $CO_2$ selectivity % | 37.7 | 26.8 | 22.4 | 20.5 |
| CO selectivity % | 14.1 | 10.0 | 9.0 | 9.2 |
| $C_2H_4$ selectivity % | 6.0 | 11.2 | 14.3 | 16.1 |
| $C_2H_6$ selectivity % | 42.2 | 52.0 | 54.3 | 54.2 |
| $C_2$ yield × 100 | 2.41 | 4.13 | 5.15 | 5.66 |

TABLE 7

| EXAMPLE | 26 | 27 | 28 | 29 |
|---|---|---|---|---|
| Temperature (°C.) | 600 | 650 | 700 | 750 |
| Flow rate (ml/min) | 947 | 947 | 947 | 947 |
| $O_2$ % in the charge | 5.0 | 5.0 | 5.0 | 5.0 |
| $CH_4$ conversion % | 3.9 | 5.3 | 6.9 | 8.7 |
| $O_2$ conversion % | 58.3 | 68.4 | 78.6 | 90.4 |
| $CO_2$ selectivity % | 22.2 | 16.7 | 14.3 | 12.3 |
| CO selectivity % | 25.5 | 20.4 | 15.7 | 12.0 |
| $C_2H_4$ selectivity % | 5.0 | 11.8 | 12.7 | 23.9 |
| $C_2H_6$ selectivity % | 47.1 | 51.1 | 57.2 | 51.8 |
| $C_2$ yield × 100 | 2.02 | 3.33 | 4.83 | 6.57 |

TABLE 8

| EXAMPLE | 30 | 31 | 32 | 33 |
|---|---|---|---|---|
| Temperature (°C.) | 600 | 650 | 700 | 750 |
| Flow rate (ml/min) | 947 | 947 | 947 | 947 |
| $O_2$ % in the charge | 5.0 | 5.0 | 5.0 | 5.0 |
| $CH_4$ conversion % | 4.1 | 6.1 | 8.7 | 9.3 |
| $O_2$ conversion % | 55.1 | 74.9 | 88.4 | 94.6 |
| $CO_2$ selectivity % | 35.3 | 22.2 | 17.5 | 14.5 |
| CO selectivity % | 19.7 | 14.5 | 10.7 | 10.0 |
| $C_2H_4$ selectivity % | 4.2 | 10.0 | 16.1 | 20.8 |
| $C_2H_6$ selectivity % | 40.8 | 53.3 | 55.7 | 54.7 |
| $C_2$ yield × 100 | 1.83 | 3.84 | 6.21 | 7.01 |

EXAMPLES 34-47

A quartz wool plug (5 mm thickness), 1.5 cc of contact bed whose contact mass is diluted with quartz particles (of a size from 0.1 to 0.2 cm), the thermometer well, an additional contact bed amount of 1.5 cc and finally a second quartz wool plug are introduced into a vertical tubular reactor made of sintered alumina, of 800 mm length and 12 mm inner diameter, placed in a tubular furnace. The lower quartz wool plug is 35 cm above the bottom of the tubular furnace and the reactor filling is completed with quartz particles.

Then, the gas mixture formed of 95% methane and 5% oxygen (by mole) is introduced at the top of the reactor at room temperature and the reactor is heated to the desired reaction temperature. When said temperature is reached, the oxygen concentration is brought to the desired value and the tests are performed.

The indicated temperatures are those measured at the hot-point of the contact bed.

The yields in percent express the partial selectivity to $C_2$ products multiplied by the converted methane fraction multiplied by 100. The reported yields do not take into account other higher hydrocarbons, particularly propane and propene, which were detected at significant concentrations by analysis of the effluent gas.

These examples illustrate the positive effect of adding an alkaline-earth metal to the rare-earth carbonate contact mass. The results relating to the oxidative coupling tests are reported in tables 9 to 12. All the tests are performed with the use of 0.3 g of the thus described carbonate contact mass, except when otherwise stated. The contact mass used in examples 34 and 35 is prepared by heating at 120° C. an acetic acid solution containing $Sr(NO_3)_2$ and $La(O_2CCH_3)_3$ 1.5 $H_2O$, in a Sr/La molar ratio of 0.2. The solution volume is reduced by aspiration with a water pump before being heated at 150° C. for 30 minutes under a pressure of 0.1 Pa. The resultant foam is crushed to fine powder and then roasted in air at 600° C. for 2 hours.

The X-ray diffraction analysis of the resultant contact mass shows the presence of a single species, $La_2O_2(CO_3)_2$, poorly crystallized. Strontium carbonate is completely amorphous when the contact mass is prepared by this method. The spectrum obtained by infra-red spectroscopy analysis of the resultant contact mass is identical to that obtained for a reference mechanical mixture of $La_2O_2(CO_3)$ and $SrCO_3$, $Sr/La=0.2$.

An amount of quartz particles is added to the 0.3 g of the so-prepared carbonate contact mass, in order to obtain a contact bed of 3 cc volume. The diluted contact mass is then introduced into the reactor as described above. The temperature of the furnace is increased to 655° C. in the presence of a gas mixture of 5% oxygen and 95% methane content by mole, the oxygen concentration being progressively increased thereafter.

The contact mass used in example 36 is prepared by mechanically mixing $Sr(O_2CCH_3)_2$ and $La(O_2CCH_3)_3$ 1.5 $H_2O$ in a Sr/La molar ratio of 0.2. The solid mixture is then roasted in air at a temperature of 600° C. for 2 hours before being used.

The X-ray diffraction analysis of the resultant contact mass shows the presence of $La_2O_2(CO_3)$ and also of $SrCO_3$, both poorly crystallized.

The contact mass used in example 37 is the same as that used in example 34. However, the contact bed is diluted with apha alumina particles particle size: 0.6 mm) instead of quartz particles.

Example 38 illustrates the fact that other alkaline-earth metals, as well as strontium, generate contact masses efficient for methane oxidizing coupling. In this example the contact mass is prepared by roasting at 550° C. in air, for 2 hours, a mechanical mixture of $CaCO_3$ and $La_2(CO_3)_3$ $8H_2O$ in a Ca/La molar ratio of 0.2.

The results of example 39 are obtained with a contact mass prepared by dissolving $ZrO(O_2CCH_3)_2$. $2H_2O$, $Sr(O_2CCH_3)_2$ and $La(O_2CCH_3)_3$. 1.5 $H_2O$. The solution is heated to 120° C., then dry-evaporated by suction with a water pump. The resultant mass is then heated for 30 minutes at 160° C. under a pressure of 0.1 Pa and roasted at 600° C. in air for 2 hours. This example shows that the addition of a group IVA metal also gives a highly active and selective mass for methane oxidative coupling.

Examples 40 and 41 are comparative examples showing that the above-described contact masses may be used in the presence of an active carrier such as $LaAlO_3$. The results of example 40 are obtained by using 1.9 g of $LaAlO_3$ of relatively high surface/area (18.4 m²/g) without deposition of rare-earth metal carbonate. The results of example 41 show that the yield is increased by adding a carbonate containing La $AlO_3$ contact mass. In this example, a solution of $Sr(O_2CCH_3)_2$ and $La(O_2CCH_3)_3$ 1.5 $H_2O$ in diluted acetic acid is used to impregnate $LaAlO_3$ by the dry impregnation technique. The so-prepared supported compound contains 10% by weight of a mixture of acetates with a Sr/La molar ratio of 0.2. The obtained compound is heated for 2 hours in air at 600° C. in order to obtain the supported carbonate contact mass. The results of example 41 (see table 10) are obtained by using 0.4 g of supported carbonate contact mass diluted with quartz particles to obtain 3 cc of contact bed.

Examples 42-44 show that the presence of steam in the charge has a positive effect on the oxidative coupling reaction in the presence of the above-described carbonate contact masses. The results of these examples have been obtained by using 0.3 g of the contact mass described above in example 34. Examples 43 and 44 indicate that the presence of steam in the charge increases the methane conversion and hence results in higher yields to $C_2$ products. In examples 43 and 44 the oxygen percent is an oxygen molar percent with respect to oxygen and methane.

The beneficial effect obtained by adding carbon dioxide to the methane- and oxygen-containing gas may be observed by comparing examples 45 and 46. The results of example 45 have been obtained by using 0.3 g of the contact mass described in example 34. In example 45, the oxygen percent is a molar percent of oxygen with respect to oxygen and methane. The results of example 46 are obtained five minutes after discontinuation of carbon dioxide addition. As observed, without carbon dioxide in the reactant gas, the contact bed temperature increases, whereas the methane conversion and the yield to $C_2$ products decrease. These results indicate that the presence of carbon dioxide in the gas reactant effectively moderates the bed temperature and increases the activity of the carbonate contact mass.

Example 47 is a comparative example identical to example 34, except that the alkaline-earth metal is absent. The results are not as good as those of example 34.

TABLE 9

| EXAMPLE | 34 | 35 | 36 | 37 |
|---|---|---|---|---|
| Bed temperature (°C.) | 873 | 940 | 765 | 790 |
| Flow rate (ml/min) | 1150 | 2300 | 1163 | 1150 |
| $O_2$ % in the charge | 13 | 13 | 14 | 13 |
| $CH_4$ conversion % | 19.5 | 19.1 | 20.3 | 19.6 |
| $O_2$ conversion % | 99.7 | 99.2 | 98.4 | 100 |
| $CO_2$ selectivity % | 20.9 | 21.2 | 23.9 | 23.2 |
| CO selectivity % | 7.1 | 9.3 | 9.9 | 7.4 |
| $C_2H_4$ selectivity % | 33.2 | 39.1 | 34.2 | 31.7 |
| $C_2H_6$ selectivity % | 38.8 | 30.4 | 32.0 | 37.7 |
| $C_2$ yield × 100 | 14.04 | 13.27 | 13.44 | 13.60 |

TABLE 10

| EXAMPLE | 38 | 39 | 40 | 41 |
|---|---|---|---|---|
| Bed temperature (°C.) | 805 | 795 | 908 | 757 |
| Flow rate (ml/min) | 1150 | 1495 | 1150 | 1150 |
| $O_2$ % in the charge | 13 | 13 | 13 | 13 |
| $CH_4$ conversion % | 19.8 | 18.9 | 16.4 | 19.4 |
| $O_2$ conversion % | 98.4 | 99.2 | 99.9 | 97.3 |
| $CO_2$ selectivity % | 21.5 | 20.8 | 32.0 | 26.4 |
| CO selectivity % | 12.3 | 7.3 | 13.1 | 10.7 |
| $C_2H_4$ selectivity % | 31.4 | 32.4 | 32.3 | 32.0 |
| $C_2H_6$ selectivity % | 34.8 | 39.5 | 22.6 | 30.9 |
| $C_2$ yield × 100 | 13.11 | 13.59 | 9.00 | 12.20 |

TABLE 11

| EXAMPLE | 42 | 43 | 44 |
|---|---|---|---|
| Bed temperature (°C.) | 841 | 854 | 861 |
| Flow rate (ml/min) $CH_4 + O_2$ | 1050 | 1050 | 1050 |
| Flow rate (ml/min) $H_2O$ | 0 | 1 | 2 |
| $O_2$ % in the charge | 13 | 13 | 13 |
| $CH_4$ conversion % | 19.2 | 19.5 | 19.5 |
| $O_2$ conversion % | 99.6 | 99.2 | 98.7 |
| $CO_2$ selectivity % | 22.4 | 21.4 | 21.4 |
| CO selectivity % | 6.6 | 6.4 | 6.7 |
| $C_2H_4$ selectivity % | 37.2 | 36.9 | 36.2 |
| $C_2H_6$ selectivity % | 33.8 | 35.3 | 35.7 |
| $C_2$ yield × 100 | 13.63 | 14.08 | 14.02 |

TABLE 12

| EXAMPLE | 45 | 46 | 47 |
|---|---|---|---|
| Bed temperature (°C.) | 816 | 856 | 873 |
| Flow rate (ml/min) $CH_4 + O_2$ | 1050 | 1150 | 1150 |
| Flow rate (ml/min) $H_2O$ | 57.45 | 0 | 0 |
| $O_2$ % in the charge | 13 | 13 | 13 |

TABLE 12-continued

| EXAMPLE | 45 | 46 | 47 |
|---|---|---|---|
| $CH_4$ conversion % | 20.4 | 19.5 | 18.3 |
| $O_2$ conversion % | 96.4 | 96.5 | 99.8 |
| $CO_2$ selectivity % | 19.1 | 21.4 | 23.0 |
| CO selectivity % | 12.0 | 9.1 | 12.8 |
| $C_2H_4$ selectivity % | 32.5 | 32.0 | 30.0 |
| $C_2H_6$ selectivity % | 36.4 | 37.5 | 34.2 |
| $C_2$ yield × 100 | 14.06 | 13.55 | 11.7 |

What is claimed as the invention is:

1. A process for converting methane to higher hydrocarbons comprising contacting at conversion conditions a mixture of methane- and oxygen-containing gas with a solid contact mass containing at least one rare-earth metal carbonate wherein the rare-earth metal is lanthanum, neodymium or samarium, and wherein the conversion conditions are such that the carbonate remains essentially carbonate during the conversion.

2. A process according to claim 1, wherein the rare-earth carbonate corresponds to $M_2O_2(CO_3)$, each M being said rare-earth group metal.

3. A process according to claim 2, wherein the rare-earth carbonate corresponds to $La_2O_2(CO_3)$.

4. A process according to claim 1, wherein the contact mass further contains an alkaline-earth metal.

5. A process according to claim 4, wherein the rare-earth metal carbonate and the alkaline-earth metal compound comply with the general formula $Z_aM_bO_{c-x}(CO_3)_x$ wherein Z represents one or more alkaline-earth metals, M represents one or more of said rare-earth metals, $a=0.001$ to 2, $b=2$, $c=3+a$ and $x=0.1$ to c.

6. A process according to claim 4, wherein the rare-earth metal carbonate and the alkaline-earth metal compound comply with the general formula $Z_aM_2O_2(CO_3)_{1+a}$ wherein a ranges from 0.001 to 2.

7. A process according to claim 1, wherein the contact mass is supported by silica, magnesia, calcium oxide, zinc oxide, alpha-alumina, a rare-earth perovskite, a spinelle or a rare-earth pyrochlore.

8. A process according to claim 1, further comprising adding 0.1 to 25% by mole of steam to the gas mixture.

9. A process according to claim 1, further comprising adding 0.1 to 20% by mole of carbon dioxide to the gas mixture.

10. A process according to claim 1, conducted at 300°–950° C. under a pressure from 1 to 100 bars and at a contact time of $10^{-6}$ to 10 seconds.

11. A process according to claim 1, conducted at a temperature from 550° to 750° C. under a pressure from 1 to 20 bars and at a contact time of $10^{-5}$ to 1 second.

12. A process according to claim 1, wherein the contact mass comprises a compound of the formula $Z_aM'_dM_bO_{c-x}(CO_3)_x$ wherein Z represents at least one alkaline earth metal, M represents at least one rare-earth metal, M' represents at least one group IVA metal, $a=0.001$ to 2, $b=2$, $c=3+a+2d-z$, $d=0.001$ to 2, $x=0.1$ to c, $z=0$ to $0.5d$.

13. A process according to claim 1, wherein the oxygen amount contained in the methane ranges from 0.1 to 40% by mol.

14. A process according to claim 1, wherein the oxygen amount contained in the methane ranges from 5 to 25% by mol.

15. A process according to claim 13, conducted at a temperature from 550° to 750° C. under a pressure from 1 to 20 bars and at a contact time of $10^{-5}$ to 1 second.

16. A process according to claim 1, wherein the contact mass further comprises a group IVA metal compound.

17. A process according to claim 4, wherein the contact mass further comprises a group IVA metal compound.

18. A process according to claim 16, conducted at a temperature from 550° to 750° C. under a pressure from 1 to 20 bars and at a contact time of $10^{-5}$ to 1 second.

19. A process according to claim 18, wherein the rare-earth carbonate corresponds to $La_2O_2(CO_3)$.

20. A process according to claim 19, further comprising adding 0.1 to 20% by mole of carbon dioxide to the gas mixture.

* * * * *